United States Patent
Haran

(10) Patent No.: US 9,439,994 B2
(45) Date of Patent: *Sep. 13, 2016

(54) ELECTRONICALLY CONTROLLED NEBULIZER

(71) Applicant: SCENTCOM LTD., Lehavot Haviva (IL)

(72) Inventor: Yossi Haran, Modiin (IL)

(73) Assignee: SCENTCOM LTD., Lehavot Haviva (IL)

( * ) Notice: Subject to any disclaimer, the term of this patent is extended or adjusted under 35 U.S.C. 154(b) by 209 days.

This patent is subject to a terminal disclaimer.

(21) Appl. No.: 14/274,738

(22) Filed: May 11, 2014

(65) Prior Publication Data

US 2014/0252106 A1    Sep. 11, 2014

Related U.S. Application Data

(63) Continuation of application No. 13/143,202, filed as application No. PCT/IL2010/000016 on Jan. 7, 2010, now Pat. No. 8,727,234.

(60) Provisional application No. 61/143,283, filed on Jan. 8, 2009.

(51) Int. Cl.
*B05B 17/04* (2006.01)
*B05B 1/08* (2006.01)
(Continued)

(52) U.S. Cl.
CPC ............. *A61L 9/122* (2013.01); *A61L 9/125* (2013.01); *A61L 9/14* (2013.01); *B05B 17/0646* (2013.01);
(Continued)

(58) Field of Classification Search
CPC ......... A61L 9/122; A61L 9/125; A61L 9/14; A61L 9/03; A61L 2209/11; A61L 2209/132; B05B 17/0646; B05B 17/0669; B05B 15/02

USPC ............. 239/4, 34, 35, 58–89, 102.1, 102.2, 239/44–45, 436, 441, 448–449
See application file for complete search history.

(56) References Cited

U.S. PATENT DOCUMENTS

| 4,695,434 A | 9/1987 | Spector |
|---|---|---|
| 4,850,534 A | 7/1989 | Takahashi et al. |

(Continued)

FOREIGN PATENT DOCUMENTS

| EP | 1329228 A1 | 7/2003 |
|---|---|---|
| EP | 1543844 A2 | 6/2005 |

(Continued)

OTHER PUBLICATIONS

International Search Report for parallel PCT application PCT/IL2010/00016, by European Patent Office of mailing date Apr. 6, 2010.

(Continued)

*Primary Examiner* — Justin Jonaitis
(74) *Attorney, Agent, or Firm* — Simon Kahn; Chanoch Kahn

(57) ABSTRACT

An electronically controlled scent producing element (800) constituted of: a plate (860) exhibiting a plurality of perforations extending from a first face of the plate to a second face of the plate opposing the first face; a plurality of micro-plugs (870) juxtaposed with the plate (860), each of the plurality of micro-plugs (870) extending longitudinally from a base end to a tip end, and arranged to mate with one of the plurality of perforations; a translation mechanism in communication with one of the (820, 860) and the plurality of micro-plugs (870); and a vibrator in communication with at least one of the plate (820, 860) and the plurality of micro-plugs.

20 Claims, 8 Drawing Sheets

(51) Int. Cl.

| | | |
|---|---|---|
| *B05B 3/04* | (2006.01) | |
| *A24F 25/00* | (2006.01) | |
| *A61L 9/12* | (2006.01) | |
| *A61L 9/14* | (2006.01) | |
| *B05B 17/00* | (2006.01) | |
| *B05B 17/06* | (2006.01) | |
| *A61L 9/03* | (2006.01) | |
| *B05B 15/02* | (2006.01) | |

(52) U.S. Cl.
CPC ............... *B05B 17/0669* (2013.01); *A61L 9/03* (2013.01); *A61L 2209/11* (2013.01); *A61L 2209/132* (2013.01); *B05B 15/02* (2013.01)

(56) References Cited

U.S. PATENT DOCUMENTS

| | | |
|---|---|---|
| 5,435,282 A | 7/1995 | Haber et al. |
| 5,972,290 A | 10/1999 | De Sousa |
| 6,024,783 A | 2/2000 | Budman |
| 6,136,277 A | 10/2000 | Nardini |
| 6,149,873 A | 11/2000 | Potter et al. |
| 6,152,829 A | 11/2000 | Jaidka |
| 6,325,475 B1 | 12/2001 | Hayes et al. |
| 6,530,370 B1 | 3/2003 | Heinonen |
| 6,536,746 B2 | 3/2003 | Watkins |
| 6,539,937 B1 | 4/2003 | Haveri |
| 6,581,915 B2 | 6/2003 | Bartsch et al. |
| 6,592,104 B2 | 7/2003 | Cox |
| 6,602,475 B1 | 8/2003 | Chiao |
| 6,656,041 B1 | 12/2003 | Kaminkow |
| 6,962,151 B1 | 11/2005 | Knoch et al. |
| 7,040,548 B2 | 5/2006 | Rodgers |
| 7,160,515 B2 | 1/2007 | Murdell et al. |
| 7,223,361 B2 | 5/2007 | Kvietok et al. |
| 7,437,061 B2 | 10/2008 | Manne |
| 8,727,234 B2 * | 5/2014 | Haran ............... A61L 9/122 239/102.2 |
| 2003/0107139 A1 | 6/2003 | Wohrle |
| 2004/0164101 A1 | 8/2004 | Cornet et al. |
| 2006/0289673 A1 | 12/2006 | Wang et al. |
| 2007/0189919 A1 | 8/2007 | Prince et al. |
| 2008/0043204 A1 | 2/2008 | Guo |
| 2008/0191370 A1 | 8/2008 | Pankhurst et al. |

FOREIGN PATENT DOCUMENTS

| | | |
|---|---|---|
| WO | 0012143 | 3/2000 |
| WO | 0232470 A1 | 4/2002 |
| WO | 03028775 A1 | 4/2003 |
| WO | 03059403 A1 | 7/2003 |
| WO | 2004105878 A1 | 12/2004 |
| WO | 2005092400 A1 | 10/2005 |
| WO | 2006058125 A2 | 6/2006 |
| WO | 2006074562 A1 | 7/2006 |

OTHER PUBLICATIONS

Written Opinion of the International Searching Authority regarding the International Search Report for parallel PCT application PCT/IL2010/00016, by European Patent Office of mailing date Apr. 6, 2010.

* cited by examiner

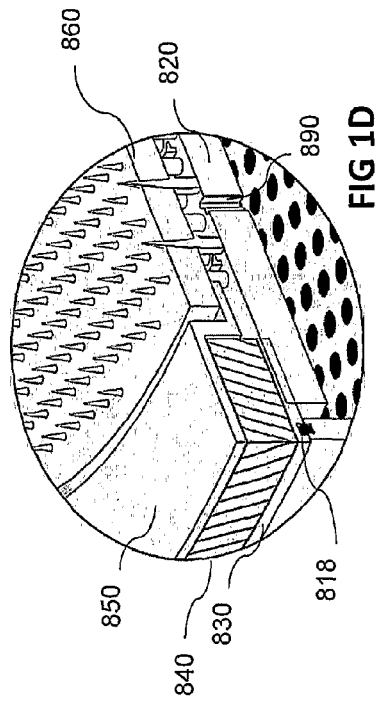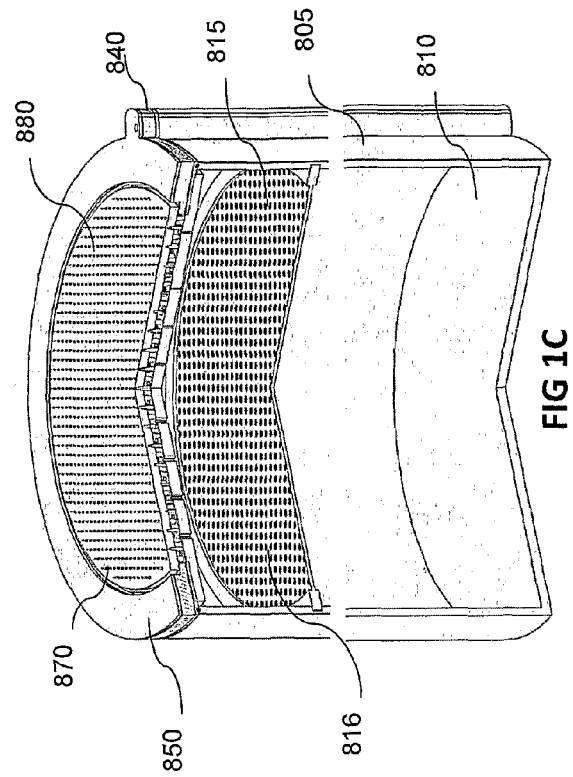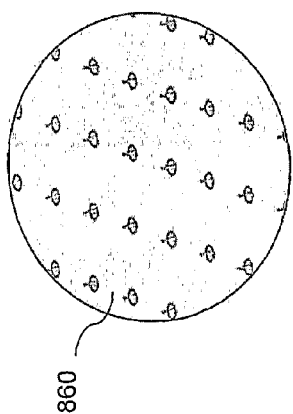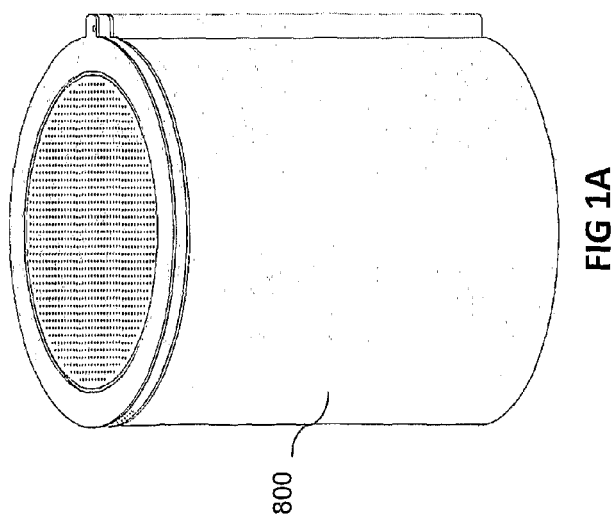

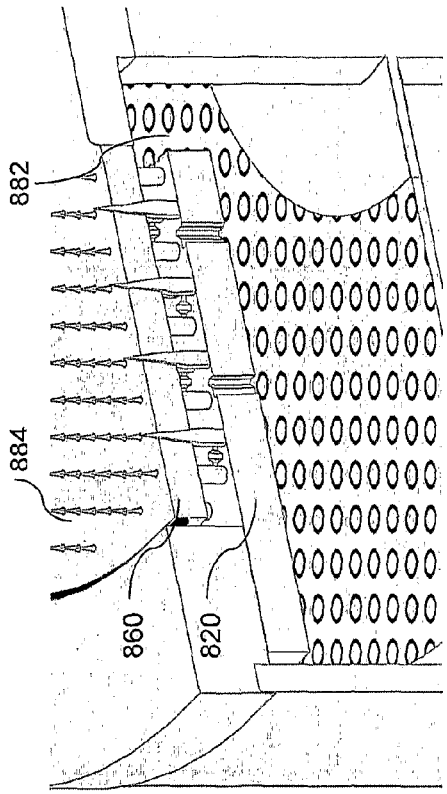
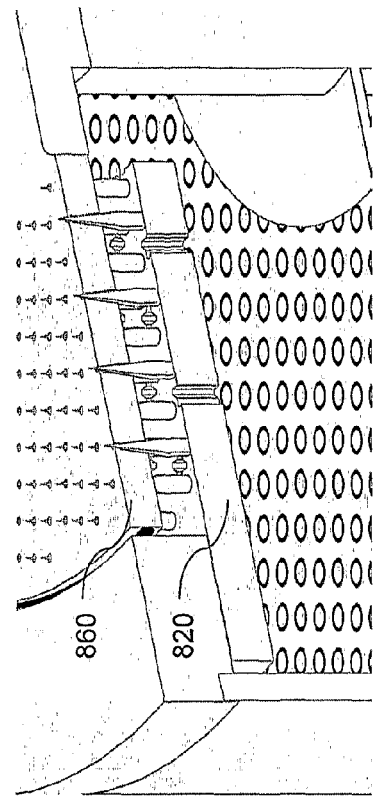
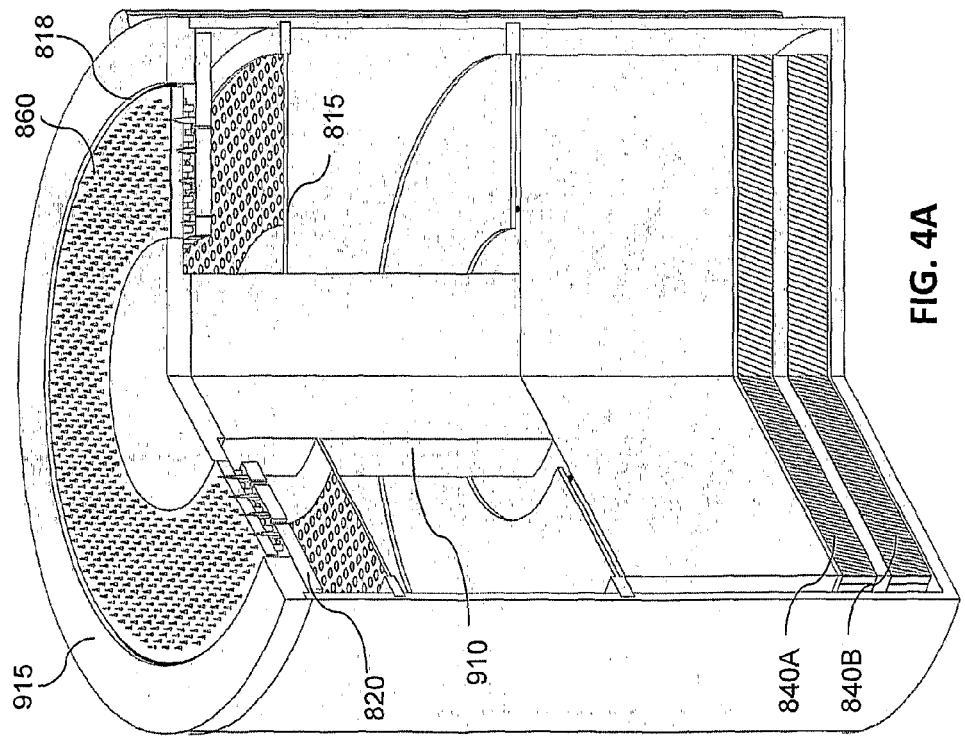

ELECTRONICALLY CONTROLLED NEBULIZER

CROSS-REFERENCE TO RELATED APPLICATIONS

This application claims priority to U.S. Provisional Patent Application Ser. No. 61/143,283 filed Jan. 8, 2009, entitled "Method and Apparatus for Computer Controlled Scent Delivery", the entire contents of which are incorporated herein by reference.

TECHNICAL FIELD

The invention relates generally to the field of electronically controlled scent production, and more particularly to an apparatus exhibiting an ultrasonic micro-plug unit.

BACKGROUND

Video games, particularly computer based games and game stations, have become extremely popular. The combination of visual and audio stimulation has succeeded in capturing a significant portion of people's leisure time. Various games have been developed, with associated hardware, that further involve the sense of touch, by allowing for varying input instruments. In one example, a musical instrument such as a mock guitar, is utilized as a game input, thus involving the sense of touch.

Games have been developed providing for a virtual reality world, again based on stimulating various user senses. However, to date, the remaining senses, namely smell and taste have not been stimulated.

U.S. Pat. No. 6,656,041 issued Dec. 2, 2003 to Kaminkow et al, the entire contents of which is incorporated herein by reference, provides for a method and apparatus for emulating a storm as part of a gaming device, preferably as a topper unit including a blower to create an air stream, an illumination source to emulate lightning, and a sound card arranged to transmit thunder. Thus, the sense of touch is stimulated, in addition to the sense of hearing and seeing.

U.S. Patent Application Publication S/N 2008/0043204 published Feb. 21, 2008 to Guo, is addressed to a digital scent movie projector with sound channels. Scent making devices release a scent into a cinema, thereby providing for film arts to provide a sense of sight, hearing and smell as part of movie.

A movie proceeds along a predetermined script, which does not allow for user interaction. Thus, the scent to be provided by Guo, are predetermined, and are not subject to change by a user action. Additionally, scent provided by Guo is arranged for releasing scent into a large space, which is not appropriate for an individual playing a computer game.

An additional problem with many prior art solutions is residual scent; particularly the scent continues to linger for a relatively long period after the desired emission. Residual scent is particularly problematic in the case of individual computer garners, which often play in undisturbed spaces, where scents easily linger. In particular, any physical element which has been contacted by a concentration of scent molecules continues to exude the scent. The residual scent further contaminates additional scents, which may need to be rapidly emitted in line with progress of the game.

World Intellectual Property Organization publication WO 02/32470 A1 published 25 Apr. 2002 to SENEIT, Inc. is addressed to an apparatus for emitting an odor. Unfortunately, the apparatus as described suffers greatly from the aforementioned residual scent, as scent molecules are deposited along the enclosed spaces of scented air travel.

Various nebulizer schemes are known to the prior art, including placing a vibrating fine mesh in contact with a liquid to be nebulized. The mesh typically is arranged to be sufficiently fine so as to block any flow of the liquid and is vibrated, typically at ultrasonic frequencies, thereby atomizing the liquid. Unfortunately, such a scheme suffers from certain drawbacks, such as spontaneous scent leakage since there is no means to prevent spontaneous release of volatile vapors via the mesh opening. Furthermore any molecules adhering to the mesh walls may be released without further vibration, further leading to residual scents. Additionally, there is a tendency for the fine mesh to become blocked by the aromatic molecules adhering to the mesh openings. Furthermore, the mesh aperture which is fixed in size is designed for a particular molecule size and viscosity, and a particular fixed mesh based nebulizer can not be used for a plurality of liquids having a range of viscosity without changing the fixed mesh.

U.S. Patent Application Publication S/N 2007/0189919 published Aug. 17, 2007 to Prince et al, the entire contents of which is incorporated herein by reference, is addressed to a method for cleaning a medicament from a portion of a nebulizer. In particular, the above mentioned application is addressed to the problem of prior art mesh based nebulizers becoming occluded.

Thus, there is a need for an electronically controlled nebulizer addressing the issue of residual scent and arranged to avoid occlusion.

SUMMARY

Accordingly, it is a principal object of the present invention to overcome at least some of the disadvantages of prior art. This is accomplished in certain embodiments by providing an electronically controlled scent producing element comprising: a plate exhibiting a plurality of perforations extending from a first face of the plate to a second face of the plate opposing the first face; a volatile scent liquid in physical contact with the first face of the plate; a plurality of micro-plugs juxtaposed with the plate, each of the plurality of micro-plugs extending longitudinally from a base end to a tip end, and arranged to mate with one of the plurality of perforations; a translation mechanism in communication with one of the plate and the plurality of micro-plugs, the translation mechanism arranged to translate the plurality of micro-plugs in relation to the plate from a first position wherein each of the plurality of micro-plugs is seated flush within a respective one of the plurality of the perforations to a second position wherein each of the plurality of micro-plugs is at least partially removed from a wall of the respective one of the plurality of perforations; and a vibrator in communication with at least one of the plate and the plurality of micro-plugs.

In one further embodiment the plurality of micro-plugs seated in the first position prevents the flow of the volatile scent liquid from the first face of the plate to the second face of the plate. In another further embodiment each of the plurality of micro-plugs exhibits a generally conically shaped taper towards the tip end. In one yet further embodiment each of the plurality of perforations are generally conically shaped, the base of the generally conically shaped plurality of perforations facing the base end of the plurality of micro-plugs. In another yet further embodiment each of the plurality of perforations exhibits a diameter of about 30 microns at the second face.

In one further embodiment the plurality of micro-plugs exhibits a shape arranged to form a ring shaped droplet towards the tip ends when the plurality of micro-plugs in relation to the plate is in the second position. In another further embodiment the translation mechanism and the vibrator are constituted of a single piezoelectric element.

In one further embodiment the vibrator is only in communication with the plurality of micro-plugs. In one yet further embodiment, the electronically controlled scent producing element further comprises a driver in communication with the translation mechanism and the vibrator, the driver arranged to translate, via the translation mechanism, the plurality of micro-plugs to the first position and vibrate the vibrator while the plurality of micro-plugs are in the first position, thereby ultrasonically cleaning the second face of the plate and the tip ends of the plurality of micro-plugs.

In one further embodiment the electronically controlled scent producing element further comprises a driver in communication with the translation mechanism and the vibrator, the driver arranged to translate, via the translation mechanism, the plurality of micro-plugs to the second position and vibrate the vibrator while the plurality of micro-plugs are in the second position, thereby atomizing the volatile scent liquid. In one yet further embodiment the driver is further arranged to detect an electrical characteristic of the vibrator, and in the event the electrical characteristic meets a predetermined value, output a signal indicative of the absence of the volatile scent liquid.

Independently the embodiments further provide for a method of electronically controlled scent production, the method comprising: providing a plate exhibiting a plurality of perforations extending from a first face of the provided plate to a second face of the provided plate opposing the first face; providing a volatile scent liquid in physical contact with the first face of the provided plate; providing a plurality of micro-plugs juxtaposed with the provided plate, each of the provided plurality of micro-plugs extending longitudinally from a base end to a tip end, and arranged to mate with one of the plurality of perforations; translating the provided plurality of micro-plugs in relation to the provided plate from a first position wherein each of the provided plurality of micro-plugs is seated flush within a respective one of the plurality of perforations to a second position wherein each of the provided plurality of micro-plugs is at least partially removed from a wall of the respective one of the plurality of perforations; and vibrating at least one of the provided plate and the provided plurality of micro-plugs with ultrasonic energy to thereby produce a scent.

In one further embodiment the provided plurality of micro-plugs seated in the first position prevents the flow of the provided volatile scent liquid from the first face of the provided plate to the second face of the provided plate. In another further embodiment each of the provided plurality of micro-plugs exhibits a generally conically shaped taper towards the tip end. In one yet further embodiment each of the plurality of perforations are generally conically shaped, the base of the provided generally conically shaped plurality of perforations facing the base end of the provided plurality of micro-plugs. In yet another further embodiment each of the plurality of perforations exhibits a diameter of about 30 microns at the second face.

In one further embodiment the translating and the vibrating are performed by a single piezoelectric element. In another further embodiment, the vibrating is only of the provided plurality of micro-plugs. In one yet further embodiment, the method further comprises ultrasonically cleaning the second face of the plate and the tip ends of the provided plurality of micro-plugs by translating the provided plurality of micro-plugs to the first position and vibrating the provided plurality of micro-plugs in the first position.

In one further embodiment the vibrating is accomplished by a vibrator, and further comprising: automatically detecting an electrical characteristic of the vibrator; and in the event the electrical characteristic meets a predetermined value, outputting a signal indicative of the absence of the provided volatile scent liquid. In one yet further embodiment the vibrating is at a frequency associated with the natural resonant frequency of the vibrator and the vibrated at least one of the provided plate and the provided plurality of micro-plugs. In one further embodiment, the method further comprises forming ring shaped droplets towards the tip ends when the provided plurality of micro-plugs in relation to the provided plate is translated to the second position.

Independently the embodiments further provide for an ultrasonic micro-micro-plug based nebulizer comprising: a plate exhibiting a plurality of perforations extending from a first face of the plate to a second face of the plate opposing the first face; a plurality of micro-plugs juxtaposed with the plate, each of the plurality of micro-plugs extending longitudinally from a base end to a tip end, and arranged to mate with one of the plurality of perforations; a translation mechanism in communication with one of the plate and the plurality of micro-plugs, the translation mechanism arranged to translate the plurality of micro-plugs in relation to the plate from a first position wherein each of the plurality of micro-plugs is seated flush within a respective one of the plurality of the perforations to a second position wherein each of the plurality of micro-plugs is at least partially removed from a wall of the respective one of the plurality of perforations; and a vibrator in communication with at least one of the plate and the plurality of micro-plugs. Preferably, a liquid is placed in physical contact with the first face of the plate.

Additional features and advantages of the invention will become apparent from the following drawings and description.

BRIEF DESCRIPTION OF THE DRAWINGS

For a better understanding of various embodiments of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawings:

FIGS. 1A-1J illustrate various views of an exemplary embodiment of an electronically controlled scent producing element comprising a plurality of micro-plugs and a perforated plate juxtaposed with the plurality of micro-plugs, in accordance with an exemplary embodiment;

FIGS. 4A-4C illustrate a third alternative embodiment for the scent producing element of FIG. 1A, in which a separate translation mechanism and vibrator are supplied, the vibrator arranged to vibrate only the perforated plate, in accordance with an exemplary embodiment;

DETAILED DESCRIPTION

Figure 1F:
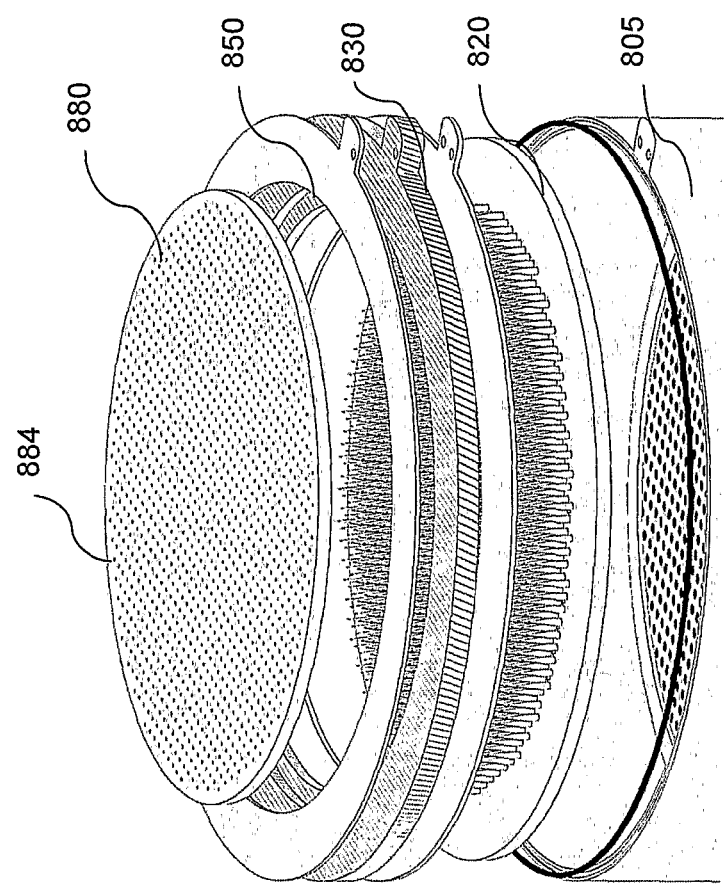

Before explaining at least one embodiment in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1E:
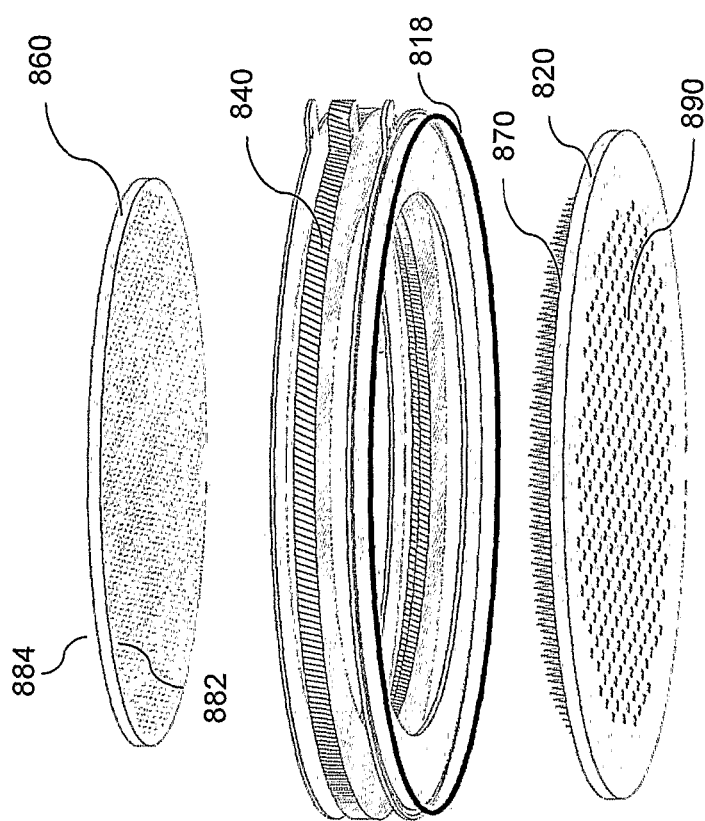
Figure 1H:
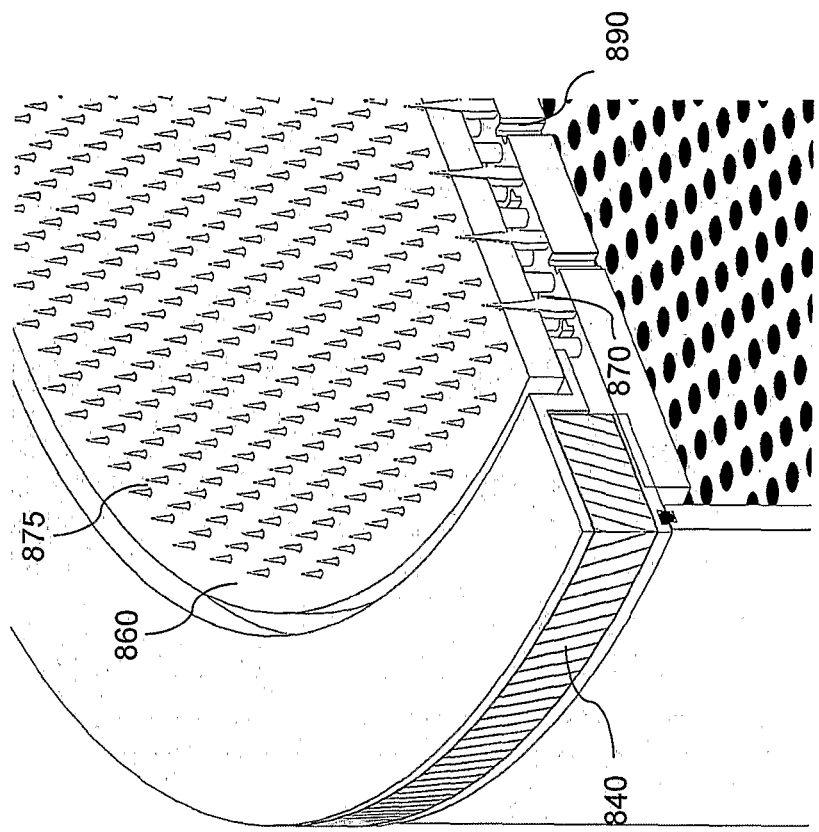
Figure 1G:
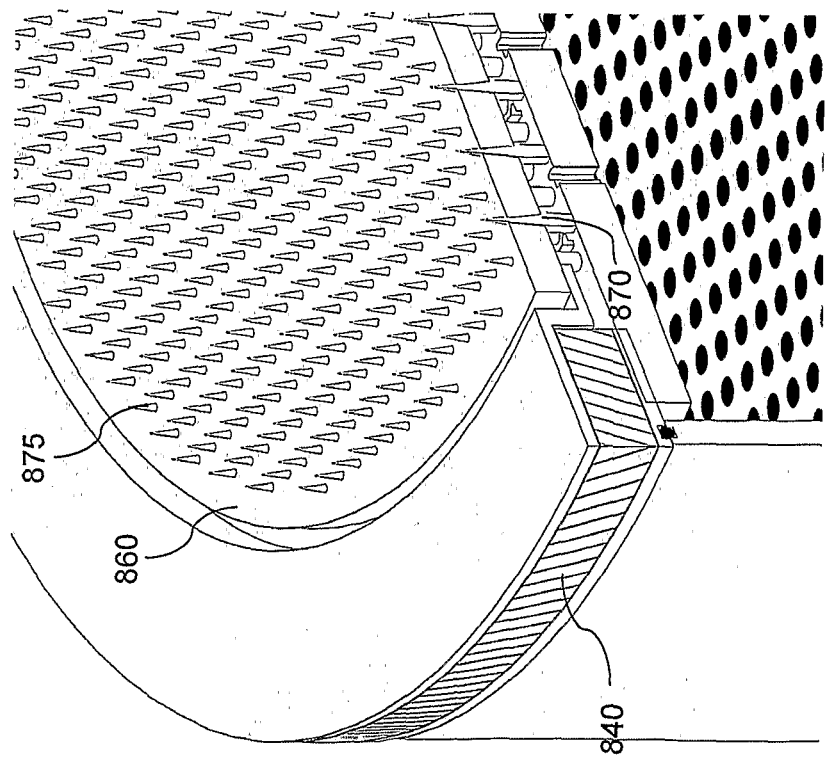
Figure 1J:
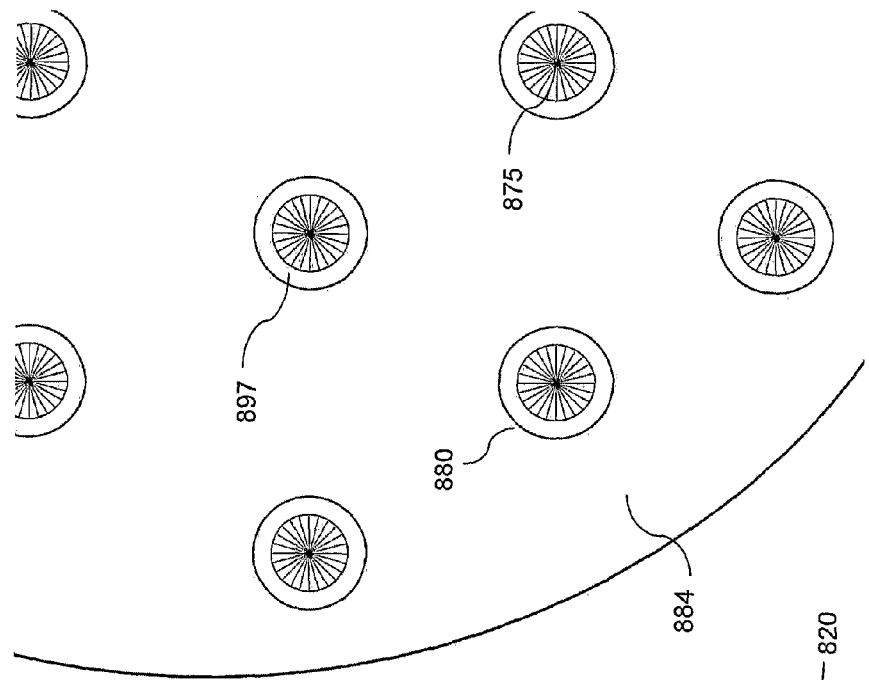
Figure 1I:
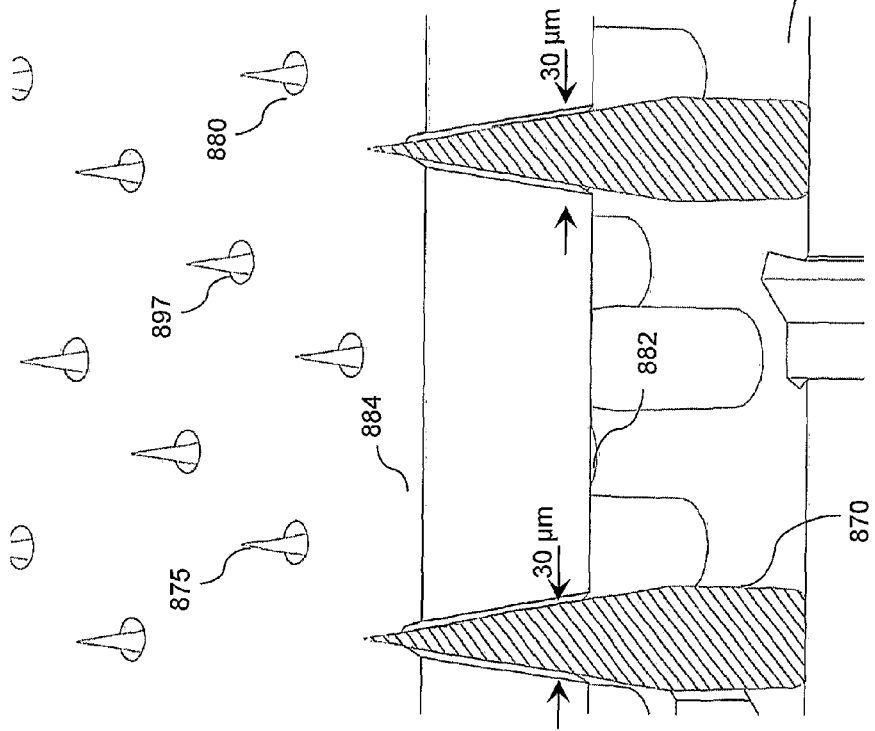

FIGS. 1A-1J illustrate various exploded views of an exemplary embodiment of an electronically controlled scent producing element 800, the views being described taken together. Electronically controlled scent producing element 800 may be used in place of electronically controlled scent producing element 130, or independently, without exceeding the scope. Electronically controlled scent producing element 800 may be further be used to nebulize, or atomize, any liquid, such as a medicament, without exceeding the scope. In particular, FIG. 1A illustrates an isometric view of electronically controlled scent producing element 800; FIG. 1B illustrates a more detailed view of a top portion of electronically controlled scent producing element 800 of FIG. 1A; FIG. 1C illustrates an isometric cut away view of electronically controlled scent producing element 800; FIG. 1D illustrates a more detailed view of the top portion of FIG. 1B; FIG. 1E illustrates a first exploded view of electronically controlled scent producing element 800; FIG. 1F illustrates a second exploded view of electronically controlled scent producing element 800; FIG. 1G illustrates a first position for certain portions of electronically controlled scent producing element 800; FIG. 1H illustrates a second position for certain portions of electronically controlled scent producing element 800; FIG. 1I illustrates a highly detailed view of the perforations and plugs of electronically controlled scent producing element 800; and FIG. 1J illustrates the resultant shape of scent producing liquid droplets, in accordance with an exemplary embodiment.

Electronically controlled scent producing element 800 comprises: a container 805; a lower reservoir 810; a unidirectional flow membrane 815; an upper reservoir 816; a sealing ring 818; a plug base 820; a first electrode 830; a piezoelectric element 840; a second electrode 850; and a plate 860. Plate 860 exhibits a plurality of perforations 880 extending from first face 882 to second face 884. Plug base 820 exhibits a plurality of pass through channels 890, and a plurality of micro-plugs 870 extending longitudinally from a base portion attached to plug base 820 to a tip end 875, with each plug arranged to mate with a respective one of perforations 880. Preferably, a portion of each plug 870, and particularly the portion extending through perforations 880 are conically shaped with an apex extending away from plug base 820. Perforations 880 are preferably similarly conically shaped, such that when plug base 820 is brought to its closest position in relation to first face 882, micro-plugs 870 are seated flush against the inner walls of the respective perforation 880. Preferably, perforations 880 exhibit a diameter of about 30 microns at first face 882, matching the diameter of micro-plugs 870 when completely seated therein. The space created towards second face 884 when each micro-plug 870 is separated from the respective perforation 880 is denoted space 895, and a ring shaped droplet 897 of volatile scent liquid is formed by the shape of plug 870 in proximity of second face 884.

Sealing ring 818 is provided of a compliant material so as to form a seal against liquid, in particular a volatile scent liquid. Unidirectional flow membrane 815, in cooperation with container 805, forms lower reservoir 810. Unidirectional flow membrane 815, in cooperation with plug base 820, forms upper reservoir 816. In particular, unidirectional flow membrane 815 defines the top of lower reservoir 810 and the bottom of upper reservoir 816. The top of upper reservoir 816 is defined by one end of plug base 820 in particular the side not exhibiting micro-plugs 870. First electrode 830 is placed at one side of piezoelectric element 840, in electrical contact therewith, and in physical contact with plug base 820, in particular the side of plug base 820 exhibiting micro-plugs 870. Piezoelectric element 840 is preferably a ring shaped element, and second electrode 850 is placed on the second side of piezoelectric element 840, in electrical contact therewith. Plate 860 is placed in physical contact with second electrode 850, and in one embodiment is secured thereto with an adhesive to prevent the escape of plate 860. Face 882 of plate 860 is juxtaposed with plug base 820 such that each micro-plug 870 extends into a matching perforation 880. The combination of micro-plugs 870 and perforations 880 forms an ultrasonic micro plug unit.

In a first mode of operation, as illustrated in FIGS. 1G and 1H, a low frequency electric power is applied to piezoelectric element 840, and in response piezoelectric element 840 expands, separating plug base 820 from plate 860 shown in FIG. 1G as being in closest proximity, to a separated position as illustrated in FIG. 1H-1J. After expansion, an additional high frequency electrical power is further supplied, superimposed on the low frequency electrical power, vibrating piezoelectric element 840. In an exemplary embodiment the high frequency electrical power exhibits a frequency range of 150-200 kHz, however this is not meant to be limiting in any way. The preferred conical shape of micro-plugs 870 function to focus the acoustical energy supplied by piezoelectric element 840 towards tip ends 875, thereby atomizing any volatile scent liquid in contact with micro-plugs 870 and within perforations 880 so as to be scented distal of second face 884. Advantageously, the conical shape of micro-plugs 870 forms ring shaped droplet 897, which requires a reduced amount of energy to atomize, or nebulize, when compared to a standard droplet of volatile scent liquid. Advantageously, the amount of separation between plug base 820 and plate 860 may be varied responsive to the viscosity of the liquid being atomized or nebulized thus varying the dimensions of the ring shaped aperture produced by micro-plugs 870 in cooperation with perforations 880, and thus a single ultrasonic micro-plug unit may be utilized for liquids having a wide range of viscosity without being blocked.

In a second mode of operation, electrical power is disconnected from piezoelectric element 840, and in response piezoelectric element 840 contracts bringing plug base 820 into closer proximity with plate 860 until micro-plugs 870 are seated flush within perforations 880, i.e. a closed position, thus sealing the volatile scent liquid from second face 884, and preventing any further scent from being experienced distal of second face 884. The particular conical shape mentioned above results in a complete seal, which is preferred for use with a volatile scent liquid, however this is not meant to be limiting in any way. In another embodiment a complete seal is not required in the second mode, but only that the plurality of micro-plugs travel sufficiently through perforations 880 to ensure that no residual liquid remains within perforations 880 to prevent occlusion.

In a third mode of operation, while micro-plugs 870 are seated flush within perforations 880, a medium to high frequency electrical power, in one non-limiting embodiment being from 40 kHz to 400 kHz, is supplied to piezoelectric element 840, thus vibrating the combination of plate 860 and micro-plugs 870. Any residual volatile scent on tip ends 875 and second face 884 is promptly atomized, or nebulized, and removed thus completely ceasing scent production.

Figure 2B:
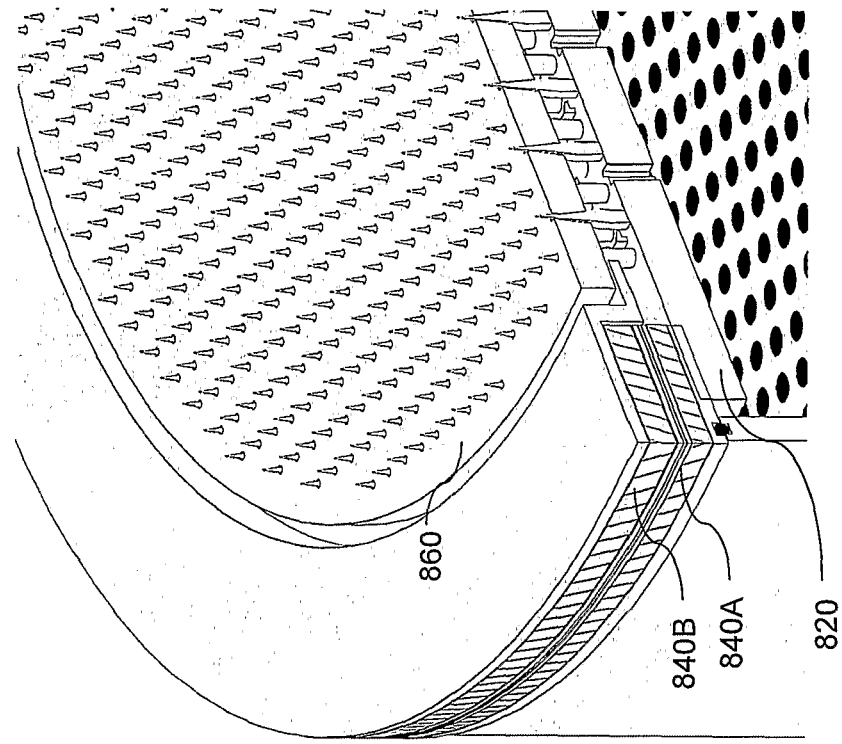
FIGS. 2A and 2B illustrate a first alternative embodiment for the scent producing element of FIG. 1A, in which a separate translation mechanism and vibrator are supplied in a stacked manner, in accordance with an exemplary embodiment.
Figure 2A:
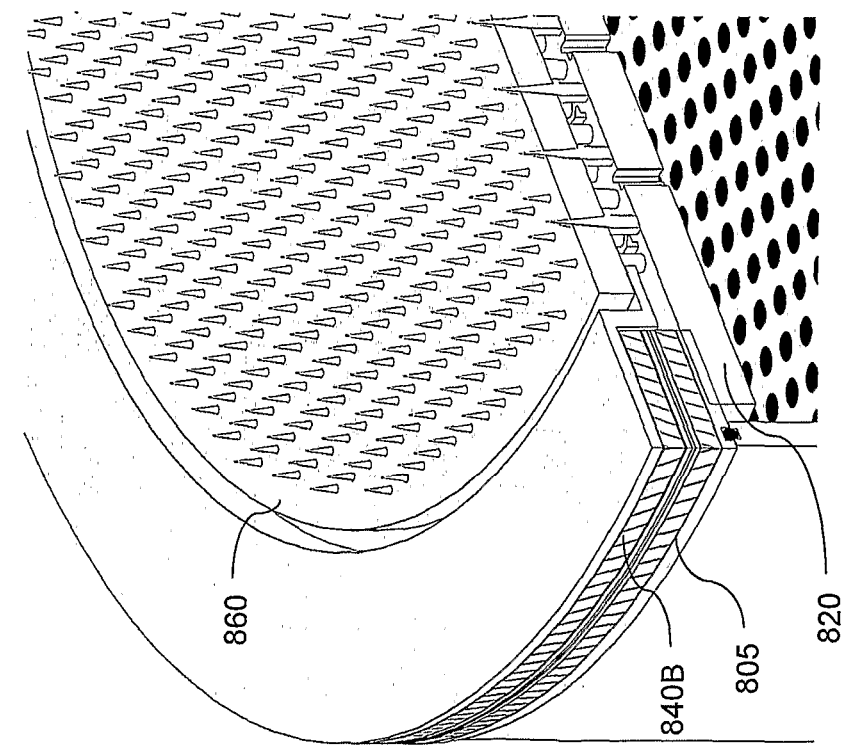

FIGS. 2A and 2B illustrate a first alternative embodiment for electronically controlled scent producing element 800, in which a plurality of elements 840 are supplied in a stacked manner, a first element being a translation mechanism 840A and a second element being a vibrator 840B. In particular, a pair of piezoelectric elements is provided, each provided with a pair of electrodes, and physically stacked. Translation mechanism 840A translates plug base 820 in relation to plate 860 between a first closed position, as shown in FIG. 2A, wherein plug base 820 is proximate plate 860 to a second open position as shown in FIG. 2B, wherein plug base 820 is removed from plate 860. Vibrator 840B operates as described above to vibrate plug base 820 and plate 860 thereby controllably producing a scent. The combination of micro-plugs 870 and perforations 880 forms an ultrasonic micro-plug unit.

Figure 3A:
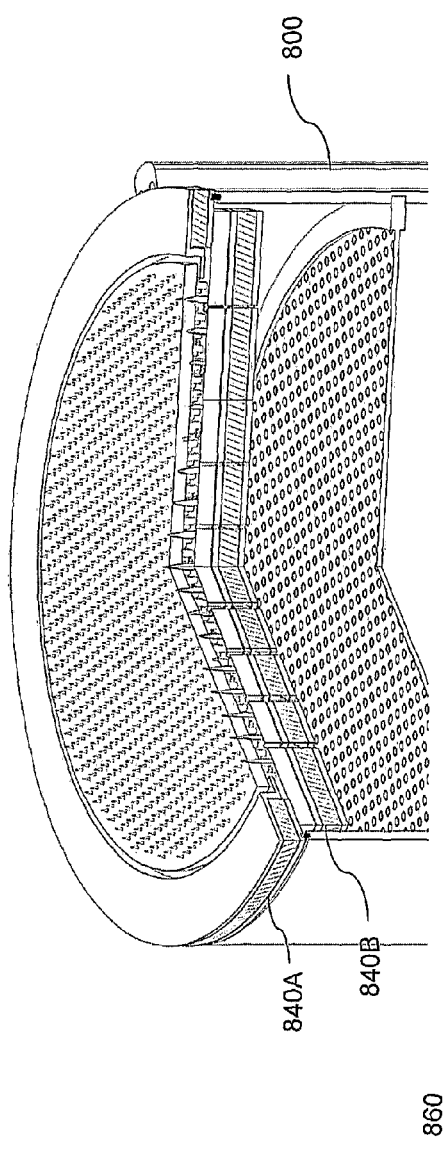
FIGS. 3A-3C illustrate a second alternative embodiment for the scent producing element of FIG. 1A, in which a separate translation mechanism and vibrator are supplied in disparate locations, in accordance with an exemplary embodiment.
Figure 3C:
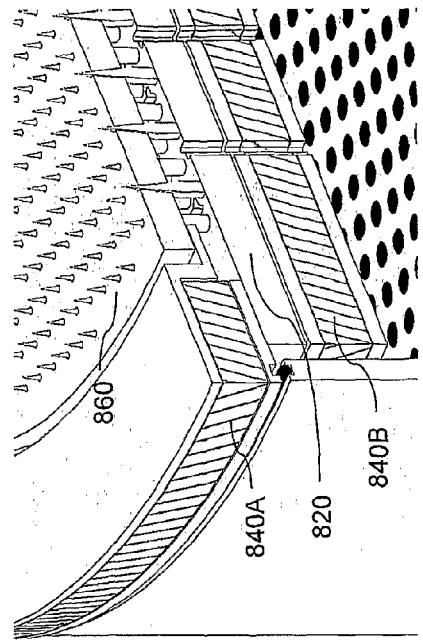
Figure 3B:
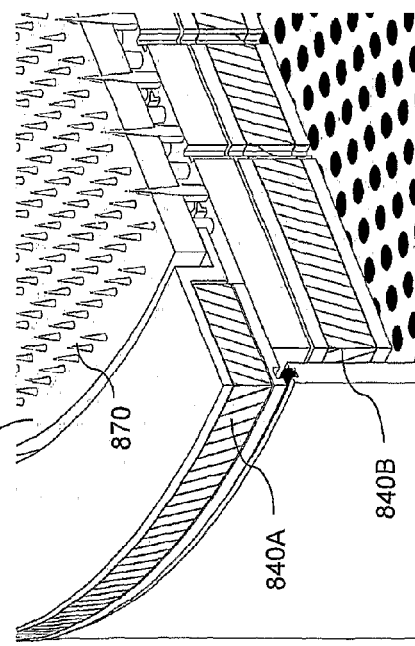
Figure 5:
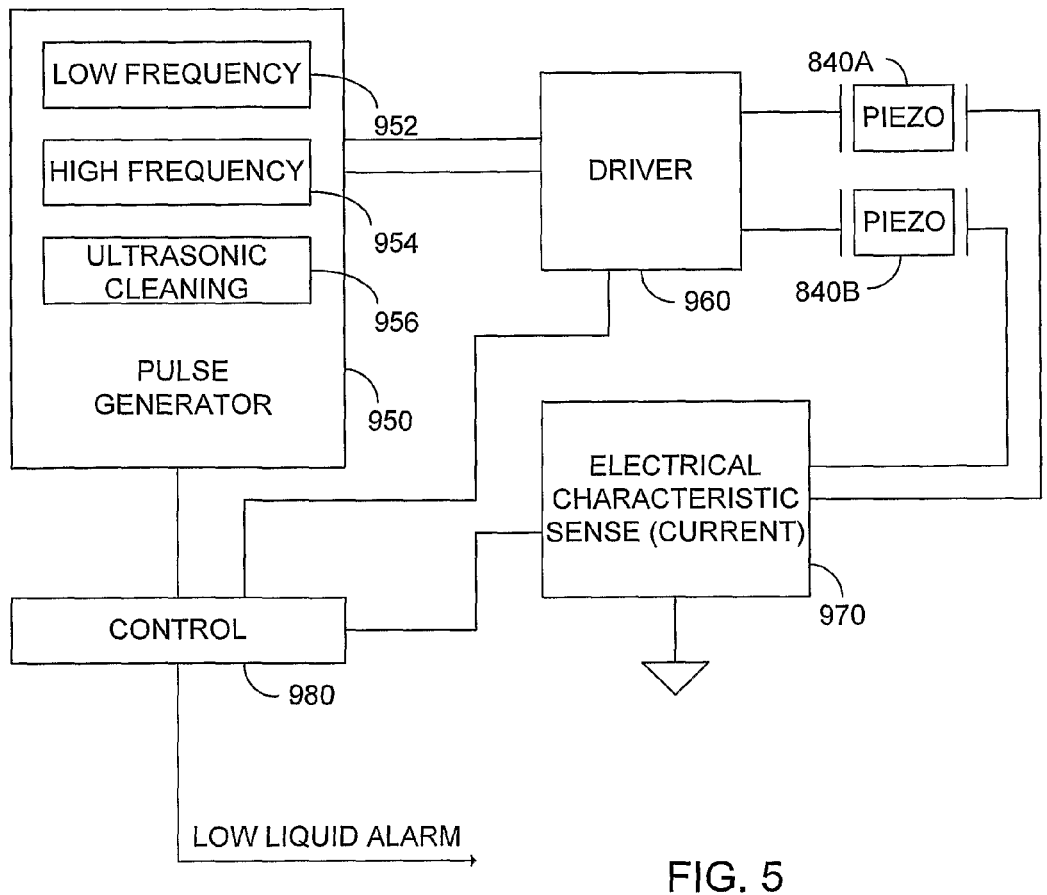
FIG. 5 illustrates a high level schematic diagram of a driving circuit useable with scent producing element 800 of any of FIGS. 1A-4C.
Figure 6:
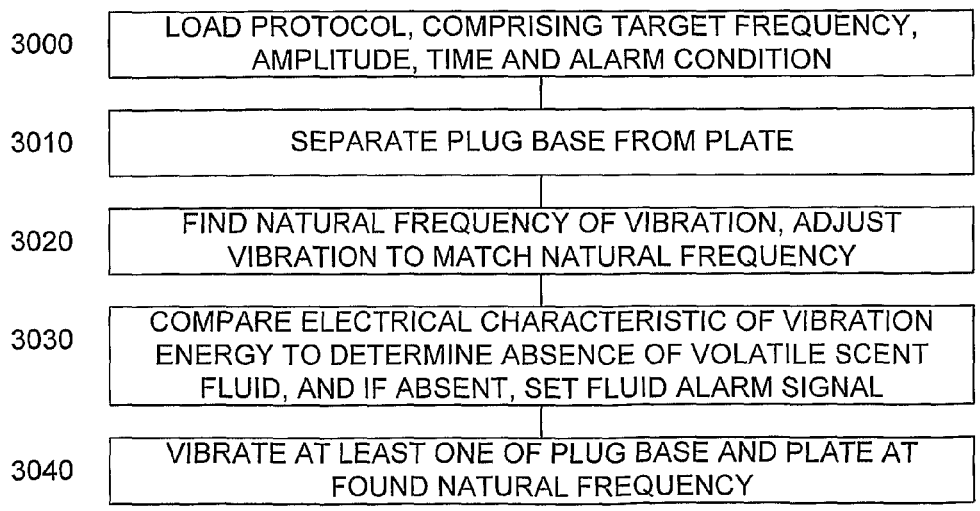
FIG. 6 illustrates a high level flow chart of the operation of control circuit of FIG. 5, in accordance with an exemplary embodiment.

FIGS. 3A-3C illustrate a second alternative embodiment for electronically controlled scent producing element 800, in which a plurality of elements 840 are supplied, a first element being a translation mechanism 840A and a second element being a vibrator 840B, in which plate 860 is fixed, and vibration energy is supplied only to plug base 820. FIG. 3A illustrates a cut away view of the second alternative embodiment, FIG. 3B illustrates the second alternative embodiment in a closed position wherein plug base 820 is proximate plate 860, and FIG. 3C illustrates the second alternative embodiment in an open position wherein plug base 820 is removed from plate 860.

In particular, plurality of elements 840 is a pair of piezoelectric elements, each provided with a pair of electrodes. Translation mechanism 840A is in communication with plate 860 and is seated against a rim of the container. Vibrator 840B is in communication with plug base 820 and mechanically isolated from plate 860. The combination of micro-plugs 870 and perforations 880 forms an ultrasonic micro-plug unit.

In a first mode of operation a low frequency electric power is applied to translation mechanism 840A, and in response translation mechanism 840A expands, separating plate 860 from base plate 820, particular by separating plate 860 from the rim of container 805. A high frequency electrical power is further supplied to vibrator 840B thus vibrating micro-plugs 870. Micro-plugs 870, exhibiting the preferred conical shape, act as a micro-acoustic lens, breaking the volatile second liquid received via pass through channels 890 into micro-drops, thus atomizing any volatile scent liquid in contact with micro-plugs 870 and within perforations 880 so as to be scented distal of second face 884.

Advantageously, as described above in relation to FIGS. 1I-1J, the shape of micro-plugs 870 are arranged to form ring shaped droplet 897, which requires a reduced amount of energy to atomize, or nebulize, when compared to a standard droplet of volatile scent liquid. In an exemplary embodiment the high frequency electrical power exhibits a frequency range of 150-200kHz, however this is not meant to be limiting in any way. Advantageously, the amount of separation between plug base 820 and plate 860 may be varied responsive to the viscosity of the liquid being atomized or nebulized thus varying the dimensions of the ring shaped aperture produced by micro-plugs 870 in cooperation with perforations 880, and thus a single ultrasonic micro-plug unit may be utilized for liquids having a wide range of viscosity without being blocked.

In a second mode of operation, electrical power is disconnected from translation mechanism 840A, and in response translation mechanism 840A contracts bringing plate 860 into closer proximity with plug base 820 until micro-plugs 870 are seated flush within perforations 880, i.e. a closed position, thus sealing the volatile scent liquid from second face 884, and preventing any further scent from being experienced distal of second face 884. The particular conical shape mentioned above results in a complete seal, which is preferred for use with a volatile scent liquid, however this is not meant to be limiting in any way. In another embodiment a complete seal is not required in the second mode, but only that the plurality of micro-plugs travel sufficiently through perforations 880 to ensure that no residual liquid remains within perforations 880 to prevent occlusion.

FIGS. 4A-4C illustrate a third alternative embodiment for electronically controlled scent producing element 800, in which a plurality of elements 840 are supplied, a first element being a translation mechanism 840A and a second element being a vibrator 840B, in which vibration energy is supplied only to plate 820 via a member 910 passing through unidirectional flow membrane 815. FIG. 4A illustrates a cut away view of the third alternative embodiment, FIG. 4B illustrates the third alternative embodiment in a closed position wherein plug base 820 is proximate plate 860, and FIG. 4C illustrates the third alternative embodiment in an open position wherein the plate 860 is moved from the plug base 820. A sealing ring 818 is further supplied providing a seal between plate 860 and a flange 915 connected to the walls of electronically controlled scent producing element 800.

In particular, plurality of elements 840, particularly translation mechanism 840A and vibrator 840B, is a pair of piezoelectric elements, each provided with a pair of electrodes. Translation mechanism 840A and vibrator 840B are each in contact with plate 860 via member 910. Vibrator 840B is mechanically isolated from plug base 820.

In a first mode of operation a low frequency electric power is applied to translation mechanism 840A, and in response translation mechanism 840A expands, separating plate 860 from base plate 820 of micro-plugs 870, to a scent producing position. A high frequency electrical power is further supplied to vibrator 840B thus vibrating plate 860 and atomizing liquid in contact with first face 882. In an exemplary embodiment the high frequency electrical power exhibits a frequency range of 150-200 kHz, however this is not meant to be limiting in any way. Advantageously, the amount of separation between plug base 820 and plate 860 may be varied responsive to the viscosity of the liquid being atomized or nebulized thus varying the dimensions of the ring shaped aperture produced by micro-plugs 870 in cooperation with perforations 880, and thus a single ultrasonic micro-plug unit may be utilized for liquids having a wide range of viscosity without being blocked.

In a second mode of operation, electrical power is disconnected from, or supplied inverted to, translation mechanism 840A, and in response translation mechanism 840A contracts, bringing plate 860 into closer proximity with plug base 820 until micro-plugs 870 are seated flush within perforations 880, i.e. a closed position, thus sealing the volatile scent liquid from second face 884, and preventing any further scent from being experienced distal of second face 884. The particular conical shape mentioned above results in a complete seal, which is preferred for use with a volatile scent liquid, however this is not meant to be limiting in any way. In another embodiment a complete seal is not required in the second mode, but only that the plurality of micro-plugs travel sufficiently through perforations 880 to ensure that no residual liquid remains within perforations 880 to prevent occlusion.

In a third mode of operation, while micro-plugs 870 are seated flush within perforations 880, a medium to high frequency electrical power, in one non-limiting embodiment being from 40 kHz to 400 kHz, is supplied to piezoelectric element 840, thus vibrating the combination of plate 860 and micro-plugs 870. Any residual volatile scent on tip ends 875 and second face 884 is promptly atomized, or nebulized, and removed thus completely ceasing scent production.

FIG. 5 illustrates a high level schematic diagram of a driving circuit useable with electronically controlled scent producing element 800 of FIGS. 1A-4C, comprising a pulse generator 950, a driver 960, a first piezoelectric element 840A and a second piezoelectric element 840B, an electrical characteristic sense circuit 970 and control circuit 980. Pulse generator 950 preferably comprises a low frequency functionality 952, a high frequency functionality 954 and an ultrasonic cleaning functionality 956. Control circuit 980 is in communication with each of pulse generator 950, driver 960 and electrical characteristic sense circuit 970. The output of pulse generator 950, which may comprise a plurality of outputs as illustrated, is connected via driver 960, to a first contact of each of first piezoelectric element 840A and second piezoelectric element 840B, respectively. The second contact of each of first piezoelectric element 840A and second piezoelectric element 840B, are respectively to electrical characteristic sense circuit 970, which may comprise a sense resistor and a comparator arranged to compare the voltage drop across the sense resistor with a value supplied by control circuit 980. In the event that a single piezoelectric element 840 is provided, one of pulse generator 950 and driver 960 are arranged to provide a combined signal to piezoelectric element 840. Alternately, as described above, a pair of electrodes are supplied at each end of the single piezoelectric element 840, a first of the pair of electrodes responsive to low frequency functionality 952 and a second of the pair of electrodes responsive to high frequency functionality 954.

In operation, and as described above, control circuit 980 operates low frequency functionality 952 to generate a low frequency electrical power, which is driven towards piezoelectric element 840 by driver 960, and is operative, for example, to separate plate 860 from base plate 820. High frequency functionality 954 is arranged to vibrate one or more of plate 860 and base plate 820. In particular modes, responsive to control circuit 980, ultrasonic cleaning functionality 956 is operative in the absence of both low frequency electrical power from low frequency functionality 952 and high frequency electrical power from high frequency functionality 954 to perform ultrasonic cleaning by providing vibrating energy to base plate 820 and plate 860 while seated flush.

Control circuit 980 is further operative to monitor at least one electrical characteristic of piezoelectric element 840 in combination with the vibrated elements, via electrical characteristic sense circuit 970. In a first mode of operation, the natural resonant frequency of piezoelectric element 840 in combination with the vibrated elements is found by sweeping, or stepping through, a range of frequencies. The natural frequency exhibits the lowest resistance to electrical current flow, and thus by monitoring the amount of current flow through piezoelectric element 840 responsive to high frequency functionality 954, the natural resonant frequency of piezoelectric element 840 in combination with the vibrated elements is found. In the event that the natural resonant frequency does not match an integer function of frequencies supplied by high frequency functionality 954, in one embodiment the frequency is toggled between one just above and just below the natural resonant frequency to achieve an average of the natural resonant frequency.

The natural resonant frequency is a function of liquid volume in communication with piezoelectric element 840, the vibrated elements, temperature and age of piezoelectric element 840. Thus, in the event that the found natural resonant frequency is indicative, due to the parameters being outside of a predetermined range, that an insufficient amount of volatile scent liquid is in communication with piezoelectric element 840, control circuit 980 is operative to assert a low liquid alarm signal.

FIG. 6 illustrates a high level flow chart of the operation of control circuit 980 of FIG. 12, in accordance with an exemplary embodiment. In stage 3000, a protocol is loaded by control circuit 980, preferably comprising a target frequency for low frequency functionality 952, a target frequency for high frequency functionality 954, a driving amplitude for driver 960, a length of time for operation, an operation mode and a low fluid alarm condition. In one non-limiting example, a scent producing protocol comprises a low frequency target value of 50 Hz, a low frequency amplitude of 20V, a high frequency target value of 159 kHz, a high frequency amplitude of 30V, a length of time of 2 seconds, and a pulsed mode of operation. In one non-limiting example, a cleaning protocol comprises a low frequency target value of 0 Hz, a low frequency amplitude of 0V, a high frequency target value of 50 kHz, a high frequency amplitude of 25V, a length of time of 6 seconds, and a continuous mode of operation. As described above the amplitude of driver 960 may be set for electrical power responsive to low frequency functionality 952, thus the amount of separation between plug base 820 and plate 860 may be varied responsive to the viscosity of the liquid being atomized or nebulized, and thus a single ultrasonic micro-plug unit may be utilized for liquids having a wide range of viscosity without being blocked.

In stage 3010, control circuit 980 is operative to separate plate 860 from plug base 820 by operating a translation mechanism. In an exemplary embodiment, the translation mechanism is a piezoelectric element 840A with a signal responsive to low frequency functionality 952. The amplitude of the low frequency signal is controlled by driver 960 responsive to the loaded protocol of stage 3000.

In stage 3020, the natural frequency of vibration is found and the frequency of vibration being driven by pulse generator 950, and in particular by high frequency functionality 954 is modified to match the natural frequency of vibration, by sweeping or steeping above and below the loaded high frequency target frequency of stage 3000. In the event that the natural resonant frequency does not match an integer function of frequencies supplied by high frequency functionality 954, in one embodiment the frequency is toggled between one just above and just below the natural resonant frequency to achieve an average of the natural resonant frequency.

In stage 3030, the electrical characteristic at the found natural frequency of vibration is compared with a predetermined range loaded as part of the protocol of stage 3000. In the event that the found natural frequency of vibration, or the electrical characteristic at the found natural frequency of vibration, is not with the predetermined range, but is instead indicative of a lack of volatile scent liquid an out of fluid alarm signal is asserted.

In stage 3040, at least one of plug base 820 and plate 860 is vibrated at the found natural frequency of stage 3020, in accordance with the operation mode and length of time of operation, loaded as part of the protocol of stage 3000.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

I claim:

1. An electronically controlled nebulizer comprising:
   a plate exhibiting a plurality of perforations extending from a first face of said plate to a second face of said plate opposing said first face;
   a plurality of micro-plugs juxtaposed with said plate, each of said plurality of micro-plugs extending longitudinally from a base end to a tip end, and arranged to mate with one of said plurality of perforations;
   a translation mechanism in communication with one of said plate and said plurality of micro-plugs, said translation mechanism arranged to translate said plurality of micro-plugs in relation to said plate from a first position, wherein each of said plurality of micro-plugs is seated within a respective one of said plurality of said perforations so as to close said respective perforation, to a second position, wherein each of said plurality of micro-plugs is at least partially removed from a wall of said respective one of said plurality of perforations so as to open said respective perforation; and
   a vibrator in communication with at least one of said plate and said plurality of micro-plugs.

2. The electronically controlled nebulizer according to claim 1, further comprising a medicament in contact with said first face of said plate.

3. The electronically controlled nebulizer according to claim 2, wherein said plurality of micro-plugs seated in said first position is closes said respective perforation sufficiently to prevent the flow of said medicament from said first face of said plate to said second face of said plate.

4. The electronically controlled nebulizer according to claim 2, wherein said plurality of micro-plugs exhibits a shape arranged to form a ring shaped droplet of said medicament towards said tip ends when said plurality of micro-plugs in relation to said plate is in said second position.

5. The electronically controlled nebulizer according to claim 2, further comprising a driver in communication with said translation mechanism and said vibrator, said driver arranged to translate, via said translation mechanism, said plurality of micro-plugs to said second position and vibrate said vibrator while said plurality of micro-plugs are in said second position, thereby atomizing said medicament.

6. The electronically controlled nebulizer according to claim 5, wherein said driver is further arranged to detect an electrical characteristic of said vibrator, and in the event said electrical characteristic meets a predetermined value, output a signal indicative of the absence of said medicament.

7. The electronically controlled nebulizer according to claim 1, wherein each of said plurality of micro-plugs exhibits a generally conically shaped taper towards said tip end.

8. The electronically controlled nebulizer according to claim 7, wherein each of said plurality of perforations are generally conically shaped, the base of said generally conically shaped plurality of perforations facing the base end of said plurality of micro-plugs.

9. The electronically controlled nebulizer according to claim 1, wherein said translation mechanism and said vibrator are constituted of a single piezoelectric element.

10. The electronically controlled nebulizer according to claim 1, wherein said vibrator is only in communication with said plurality of micro-plugs, and wherein the electronically controlled nebulizer further comprises a driver in communication with said translation mechanism and said vibrator, said driver arranged to translate, via said translation mechanism, said plurality of micro-plugs to said first position and vibrate said vibrator while said plurality of micro-plugs are in said first position, thereby ultrasonically cleaning said second face of said plate and said tip ends of said plurality of micro-plugs.

11. The electronically controlled nebulizer according to claim 1, wherein said plurality of micro-plugs in said first position are seated flush within a respective one of said plurality of said perforations.

12. A method of electronically nebulizing, the method comprising:

providing a plate exhibiting a plurality of perforations extending from a first face of said provided plate to a second face of said provided plate opposing said first face;

providing a medicament in physical contact with said first face of said provided plate;

providing a plurality of micro-plugs juxtaposed with said provided plate, each of said provided plurality of micro-plugs extending longitudinally from a base end to a tip end, and arranged to mate with one of said plurality of perforations;

translating said provided plurality of micro-plugs in relation to said provided plate from a first position wherein each of said provided plurality of micro-plugs is seated within a respective one of said plurality of perforations so as to close said respective perforation to a second position wherein each of said provided plurality of micro-plugs is at least partially removed from a wall of said respective one of said plurality of perforations so as to open said respective perforation; and vibrating at least one of said provided plate and said provided plurality of micro-plugs to thereby nebulize a portion of said medicament.

13. A method according to claim 12, wherein said provided plurality of micro-plugs seated in said first position sufficiently close said respective perforation so as to prevent the flow of said provided medicament from said first face of said provided plate to said second face of said provided plate.

14. A method according to claim 12, wherein each of said provided plurality of micro-plugs exhibits a generally conically shaped taper towards said tip end.

15. A method according to claim 14, wherein each of said plurality of perforations are generally conically shaped, the base of said provided generally conically shaped plurality of perforations facing the base end of said provided plurality of micro-plugs.

16. A method according to claim 12, wherein said translating and said vibrating are performed by a single piezoelectric element.

17. A method according to claim 12, wherein said vibrating is only of said provided plurality of micro-plugs, and wherein the method further comprises:

ultrasonically cleaning said second face of said plate and said tip ends of said provided plurality of micro-plugs by translating said provided plurality of micro-plugs to said first position and vibrating said provided plurality of micro-plugs in said first position.

18. A method according to claim 12, wherein said vibrating is accomplished by a vibrator, and further comprising:

automatically detecting an electrical characteristic of said vibrator; and in the event said electrical characteristic meets a predetermined value, outputting a signal indicative of the absence of said provided medicament.

19. A method according to claim 18, wherein said vibrating is at a frequency associated with the natural resonant frequency of said vibrator and said vibrated at least one of said provided plate and said provided plurality of micro-plugs.

20. A method according to claim 12, further comprising forming ring shaped droplets towards said tip ends when said provided plurality of micro-plugs in relation to said provided plate is translated to said second position.

* * * * *